United States Patent
Aebi et al.

(10) Patent No.: US 9,510,815 B2
(45) Date of Patent: Dec. 6, 2016

(54) METHOD AND APPARATUS FOR THE REMOVAL OF INTERVERTEBRAL DISCS

(71) Applicant: GEHRING CUT AG, Matzingen (CH)

(72) Inventors: Max Aebi, Bern (CH); Joel Hungerbuhler, Warth-Weiningen (CH); Patrik Naf, Munchwilen (CH)

(73) Assignee: GEHRING CUT AG, Matzingen (CH)

( * ) Notice: Subject to any disclaimer, the term of this patent is extended or adjusted under 35 U.S.C. 154(b) by 695 days.

(21) Appl. No.: 13/872,775

(22) Filed: Apr. 29, 2013

(65) Prior Publication Data

US 2014/0324055 A1  Oct. 30, 2014

(51) Int. Cl.
    A61B 17/70     (2006.01)
    A61B 17/02     (2006.01)
    A61B 17/00     (2006.01)

(52) U.S. Cl.
    CPC ....... *A61B 17/0293* (2013.01); *A61B 17/0206* (2013.01); *A61B 2017/00261* (2013.01)

(58) Field of Classification Search
    CPC . A61B 17/16; A61B 17/1655; A61B 17/1657; A61B 17/1662; A61B 17/1671; A61B 2017/564; A61B 17/88; A61B 17/02; A61B 17/0218; A61B 2017/0256
    See application file for complete search history.

(56) References Cited

U.S. PATENT DOCUMENTS

| | | | | |
|---|---|---|---|---|
| 6,949,105 B2* | 9/2005 | Bryan | .................... | A61B 17/02 606/130 |
| 8,100,828 B2* | 1/2012 | Frey | .................. | A61B 17/0293 600/234 |
| 8,114,019 B2* | 2/2012 | Miles | ...................... | A61B 1/32 600/202 |
| 8,211,012 B2* | 7/2012 | Wing | .................. | A61B 17/0206 600/210 |
| 2004/0230191 A1* | 11/2004 | Frey | .................... | A61B 17/0293 606/57 |
| 2008/0097164 A1* | 4/2008 | Miles | ...................... | A61B 1/32 600/219 |
| 2012/0116517 A1 | 5/2012 | Petit et al. | | |

* cited by examiner

*Primary Examiner* — Anu Ramana
(74) *Attorney, Agent, or Firm* — Rankin, Hill & Clark LLP

(57) ABSTRACT

A method for the removal of an intervertebral disc or parts thereof to be treated that includes: inserting a first longitudinal bone anchor into a pedicle of a first vertebra; inserting a second longitudinal bone anchor into a pedicle of a second vertebra; bridging the first and second anchors using a bridging element including a first and second clamp; attaching adjustable extension arms to each of the two clamps; introducing a longitudinal guiding element into the intervertebral disc or the subchondral bone of one of the vertebral bodies adjacent of intervertebral disc; fixing a retractororthogonally on the longitudinal guiding element; connecting the free ends extension arms to the retractor; immobilizing the extension arms to obtain a rigid assembly; and using the retractor as an anatomically positioned platform for performing the removal of the intervertebral disc to be treated or parts thereof, and a kit and apparatus for performing the method.

15 Claims, 23 Drawing Sheets

METHOD AND APPARATUS FOR THE REMOVAL OF INTERVERTEBRAL DISCS

BACKGROUND OF INVENTION

Field of Invention

The present invention relates to a method for the removal of intervertebral discs, to a kit for the removal of intervertebral discs and to an apparatus for the removal of intervertebral discs.

Description of the Related Art

A method for performing an intervertebral disc replacement and for anatomically establishing a reference point for an intervertebral disc to be replaced is known from Petit et al., Pub. No. US 2012/0116517 A1. In a first step bone anchors are anchored in the same vertebra, then in a second step, a linking bar is positioned between the two bone anchors and in a third step a platform is mounted on the linking bar. After adjusting and locking the position of a viewing element arranged on the platform an implantation instrument can be rotatably coupled to a rod affixed on the viewing element. This implantation instrument permits to implant a disc prosthesis or an osteosynthesis cage through a posterior, a postero-lateral or a lateral approach. One problem associated with the above described method is that the posterior or postero-lateral approach to the intervertebral disc space is achieved by means of a curved tubular implantation instrument which is pivotably coupled to the viewing element and which permits only a small operation field defined by the inner diameter of the tubular instrument. Furthermore, due to the curvature of the implantation instrument flexible instruments must be used. A further problem associated with the above described method is that the complete apparatus comprising the linking bar, the platform and the viewing element is attached to the actual vertebra by means of two pin like bone anchors.

BRIEF SUMMARY OF THE INVENTION

It is therefore an object of the invention to provide a method for the removal of intervertebral discs which permits a linear lateral or postero-lateral approach to the intervertebral disc space for inserting an artificial disk, prosthesis or cage therein. It is a further object of the invention to provide an apparatus for the removal of intervertebral discs which permits to adjust the operation field to a desired size.

The invention solves the posed problem with a method for the removal of intervertebral discs as disclosed and claimed herein, with a kit for the removal of intervertebral discs as disclosed and claimed herein and with an apparatus for the removal of intervertebral discs as disclosed and claimed herein.

The advantages of the method and apparatus according to the invention are essentially to be seen therein that:
- the retractor permits a linear lateral or postero-lateral approach to the intervertebral disc space so that no flexible instruments are required;
- due to the adjustable extension arms and the longitudinal guiding element the retractor can be exactly positioned with a desired angle with respect to the sagittal plane of the patient;
- the movable sliders of the retractor permit to reduce or enlarge the size of the operation field. The maximum size of the operation field is defined by the diameter of the through hole in the frame of the retractor; and
- a stable fixation of the longitudinal bone anchors in the pedicles can be achieved.

This is particularly important in the case of elderly patients where the pedicles provide regions with optimal bone quality.

Further advantageous embodiments of the invention can be commented as follows:

In a special embodiment the longitudinal guiding element is a Kirschner-wire or a bone pin.

In a further embodiment the longitudinal guiding element comprises a navigational tool.

Preferably, four or more longitudinal bone anchors are inserted into the pedicles of the first and second vertebrae.

In another embodiment the longitudinal bone anchors are inserted into the transition zone of the superior facet joint of the vertebra.

In again another embodiment the longitudinal bone anchors are inserted into the neck of the facet joint.

In a further embodiment the longitudinal bone anchors and the longitudinal guiding element are inserted subcutaneously.

In a further embodiment the method comprises a further step: using the retractor as an anatomically positioned platform for implanting an artificial disc or an osteosynthetic cage into the intervertebral space of the removed intervertebral disc.

In again a further embodiment the method comprises after insertion of the first and second longitudinal bone anchors into the pedicles of the first and second vertebrae the further step of: spreading the first and second bone anchors to therewith move the two adjoining vertebrae further apart by using a spreader to enlarge the intervertebral space, particularly for facilitating insertion of an intervertebral disc replacement implant or of an intervertebral implant.

In another embodiment the hinge of the bridging element is loosenably locked.

In another embodiment the method further comprises, before a retractor is fixed orthogonally on a longitudinal guiding element, the step of fitting a first tubular dilatator onto the longitudinal guiding element.

Preferably, the method additionally comprises the step of subsequently and telescopically pushing one or more further tubular dilatators over the first dilatator. Therewith, the advantage can be achieved that the tubular dilatators permit to open the operation field to a desired extent.

In a further embodiment the method further comprises, after using the retractor as an anatomically positioned platform for performing the removal of the intervertebral disc to be treated or parts thereof, the step of pulling or pushing sliders which are slideably arranged on the retractor towards or away from the guiding element until a desired opening as an operation field is achieved.

In a further embodiment the method comprises the additional step of inserting extension blades in blades attached to the sliders of the retractor.

In again a further embodiment the method comprises the additional step of inserting a pin in each extraction blade to affix the same in position relative to the retractor.

According to a further aspect of the invention, there is provided a kit for the removal of intervertebral discs or parts thereof and for the implantation of disc prosthesis or osteosynthesis cages, the kit comprising: a) two or more longitudinal bone anchors; b) one or more bridging elements comprising a first and second clamp connected by a hinge; c) two or more adjustable extension arms attachable to the clamps; d) one or more longitudinal guiding elements; and e) one or more retractors.

In a special embodiment the kit further comprises one or more dilatators which are slideable over the guiding element, respectively over the previous dilatator.

In another embodiment the kit further comprises two or more pins for fixation of extension blades of the retractor to bone.

In accordance with again a further aspect, an apparatus for the removal of intervertebral discs is provided which comprises:
- at least two longitudinal bone anchors affixable to a pedicle each;
- a bridging element comprising a first and a second clamp, wherein each clamp of the bridging element is loosenably affixed to one bone anchor;
- at least a first and a second adjustable extension arm, wherein each one end of the extension arms is loosenably affixed to one of the first and second clamps;
- a retractor which is loosenably affixed to the other ends of the extension arms, wherein the retractor comprises:
- a frame which defines a plane and a central axis orthogonal to the plane and which includes a lower side directed towards a vertebra, an upper side and a through hole coaxially to the central axis; and
- at least two sliders which are slideably arranged at the frame on opposite sides and parallel to the plane defined by the frame so as to be moved towards and away from the central axis and which are loosenably fixable relative to the frame in a desired position.

In another embodiment each extension arm comprises at least one articulation which is reversibly lockable.

In another embodiment a blade is attached to each slider so that each blade protrudes from the lower side of the frame essentially parallel to the central axis.

In again another embodiment the at least one bridging element comprises a hinge connecting the first and second clamp.

In a further embodiment the hinge of the at least one bridging element is reversibly lockable.

In another embodiment the apparatus further comprises extension blades whereof each one is loosenably affixable to one of the blades of the retractor.

Preferably, each slider comprises teeth arranged along a longitudinal side of the slider, wherein the longitudinal side extends from an inner end of the slider directed towards the central axis to an opposite outer end of the slider; and wherein the frame comprises a guidance each for the sliders which is provided with a pawl resiliently biased into engagement with the teeth of the respective slider.

In another embodiment the apparatus additionally comprises one or more cross beams each comprising a first and a second clamp connected by a hinge, wherein each clamp of the one or more cross beams is loosenably affixable to one bone anchor.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

BRIEF DESCRIPTION OF THE DRAWINGS

Several embodiments of the invention will be described in the following by way of example and with reference to the accompanying drawings in which.

DETAILED DESCRIPTION OF THE INVENTION

Figure 1:
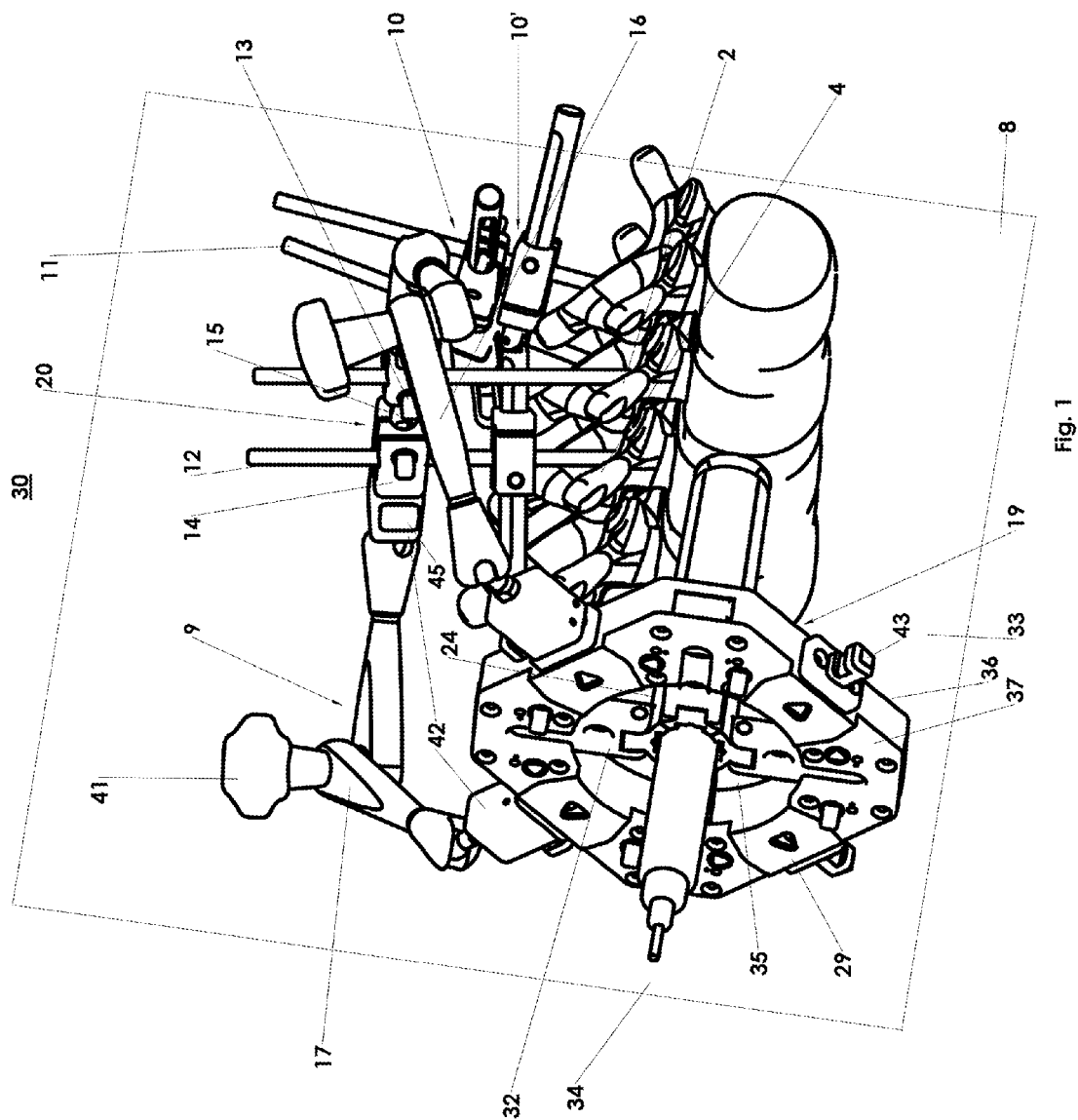
FIG. 1 illustrates a perspective view from lateral of an embodiment of the apparatus according to the invention from lateral.

The terms "comprises", "comprising", "includes", "including", "having" and their conjugates mean "including but not limited to". This term encompasses the terms "consisting of" and "consisting essentially" of.

The phrase "consisting essentially of" means that the method may include additional steps, but only if the additional steps do not materially alter the basic and novel characteristics of the claimed method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements. As used herein the term "method" refers to manners, means, techniques and procedures for accomplishing a given task including, but not limited to, those manners, means, techniques and procedures either known to, or readily developed from known manners, means, techniques and procedures by practitioners of the medical arts.

The word "optionally" is used herein to mean "is provided in some embodiments and not provided in other embodiments". Any particular embodiment of the invention may include a plurality of "optional" features unless such features conflict.

FIGS. 1 to 16 illustrate an embodiment of the apparatus 30 according to the invention essentially including a retractor 19 which is loosenably affixed to each one end of two extension arms 16, 17, a bridging element 20 to which the other ends of the extension arms 16, 17 are affixed and a plurality of bone anchors 11, 12. Exemplarily, two longitudinal bone anchors 11, 12 are affixed to each a pedicle 2, 4 of a first and a second vertebra 6, 7 (FIG. 2) on the same side of the sagittal plane 8 and two further longitudinal bone anchors 11', 12' are affixed to each a pedicle 3, 5 of the first and second vertebrae 6, 7 on the other side of the sagittal plane 8.

The bridging element 20 comprises a first and a second clamp 13, 14 and a hinge 15 arranged between the first and second clamps 13, 13. Each clamp 13, 14 of the bridging element 20 is loosenably affixed to one bone anchor 11, 12. Each one end of the extension arms 16, 17 is loosenably affixed to one of the first and second clamps 13, 14 of the bridging element 20.

The extension arms 16, 17 each comprise a centrally positioned articulation 9 which is reversibly lockable by means of a turning knob 41. Furthermore, each end of the extension arms 16, 17 is provided with a ball-and-socket joint 38 and terminally arranged a snap-on mounting 42 that can be mounted to respective pegs 43 (FIG. 3) which are terminally positioned at the clamps 13, 14 of the bridging element 20. To avoid a relative rotation between the extension arms 16, 17 and the clamps 13, 14 of the bridging element 20 the pegs 43 and the complementary cavities (not shown) in the snap-on mountings 42 have a polygonal cross section. The snap-on mountings 42 can be detached from the pegs 43 by pushing a push-button 45 provided on the snap-on mounting 42.

Figure 2:
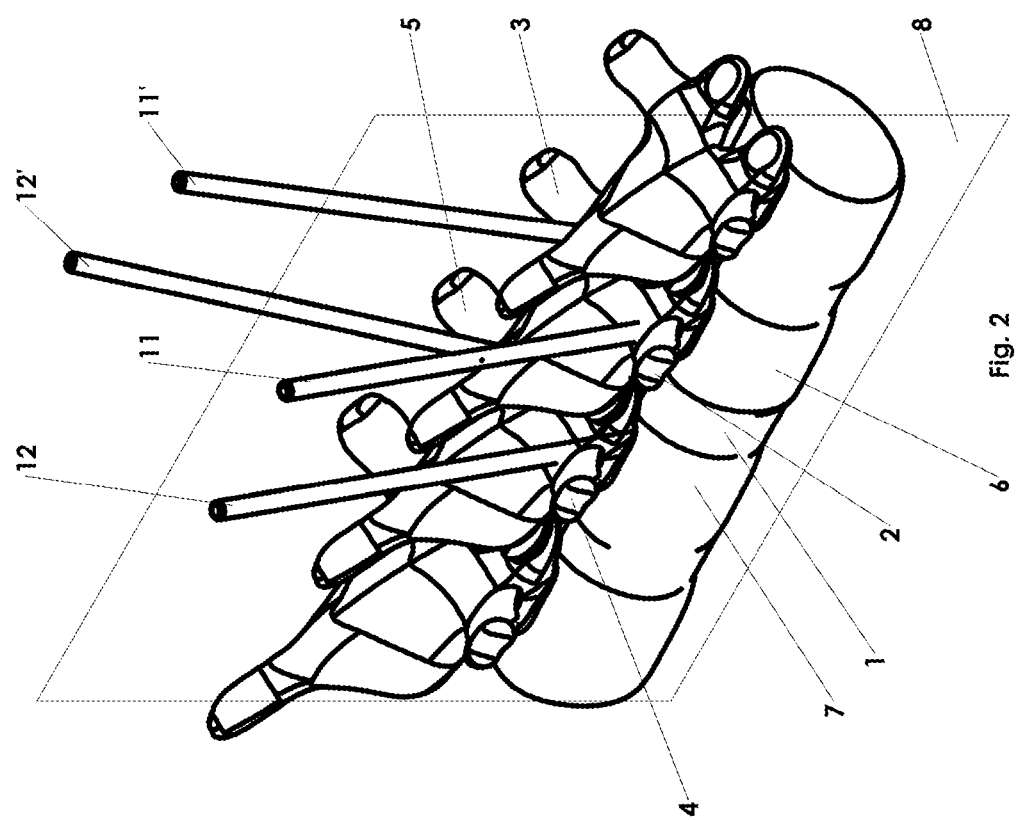
FIG. 2 illustrates a perspective view from dorsal-lateral of a portion of the spinal column with pedicle pins inserted according to a first step of an embodiment of the method according to the invention.
Figure 3:
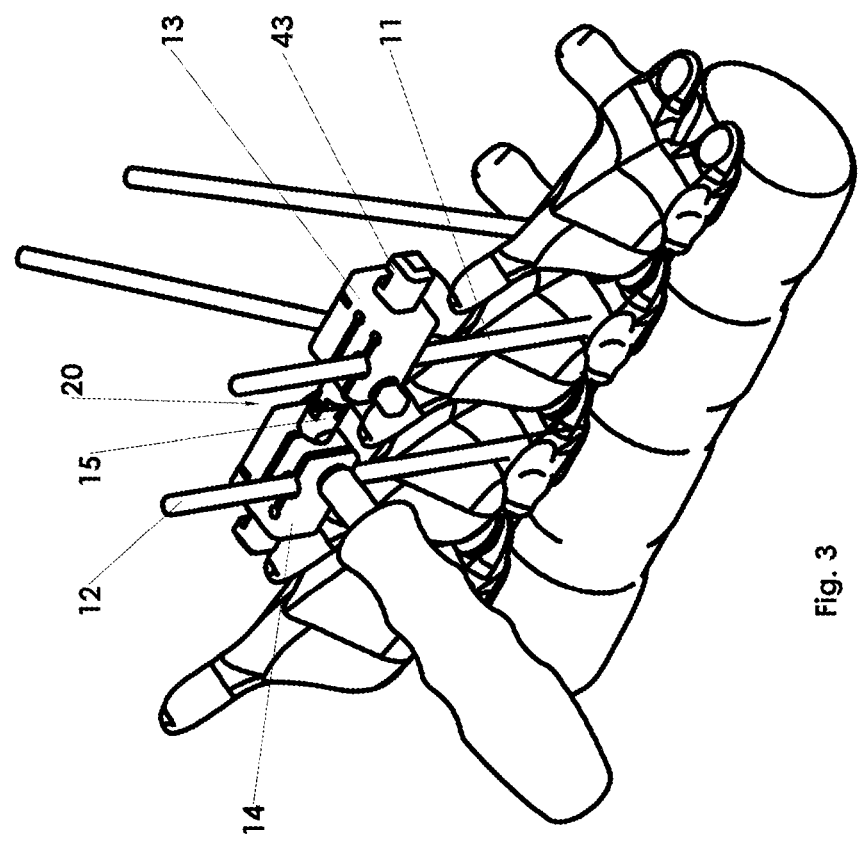
FIG. 3 illustrates a perspective view from dorsal-lateral of a portion of the spinal column with a clamp fitted to a part of the pedicle pins according to a second step of the embodiment of the method according to the invention.
Figure 4:
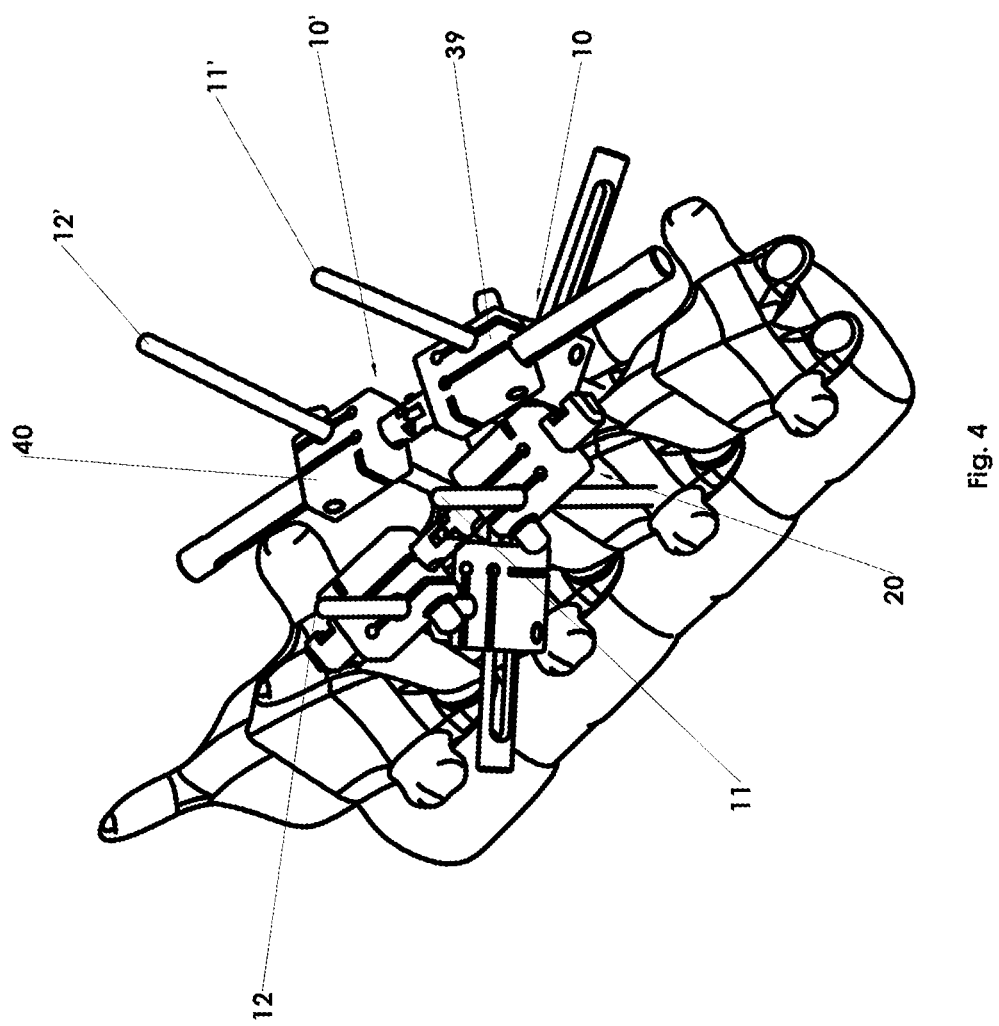
FIG. 4 illustrates a perspective view from dorsal of a portion of the spinal column with two cross beams according to the embodiment of the method according to the invention.

Additionally, a first and a second cross beam 10, 10' are attached to the bone anchors 11, 11', 12, 12'. Each cross beam 10, 10' comprises a first and a second clamp 39, 40 which are connected by a hinge 15. Exemplarily, the first cross beam 10 is attached to the first bone anchor 11' on the side of the sagittal plane 8 which is opposite to the bridging element 20 and to the second bone anchor 12 which is on the same side of the sagittal plane 8 as the bridging element 20. The second cross beam 10' is attached to the second pair of longitudinal bone anchors 11', 12' which is affixed to the pedicles 3, 5 of the first and second vertebrae 6, 7 on the side of the sagittal plane 8 which is opposite to the bridging element 20 (FIGS. 2 to 4).

The retractor 19 essentially comprises a frame 29 which defines a plane 33 and a central axis 34 orthogonal to the plane 33 and which includes a lower side 36 directed towards a vertebra, an upper side 37 and a through hole 35 coaxially to the central axis 34. Further, the retractor 19 comprises exemplarily four sliders 32 which are slideably arranged at the frame 29 on opposite sides and parallel to the plane 33 defined by the frame 29. The sliders 32 can be moved towards and away from the central axis 34 and are loosenably fixable relative to the frame 29 in a desired position. Each slider 32 is provided with teeth 44 (FIG. 11) arranged along a longitudinal side of the slider 32, extending from an inner end of the slider 32 directed towards the central axis 34 to an opposite outer end of the slider 32. The frame 29 comprises a guidance each for the sliders 32 which is provided with a pawl (not shown) resiliently biased into engagement with the teeth 44 of the respective slider 32. Furthermore, the frame 29 is provided with similar pegs 43 as the clamps 13, 14 of the bridging element 20 so that the snap-on mountings 42 on the other ends of the extension arms 16, 17 can be attached to the pegs 43 on the frame 29 of the retractor 19.

Figure 22:
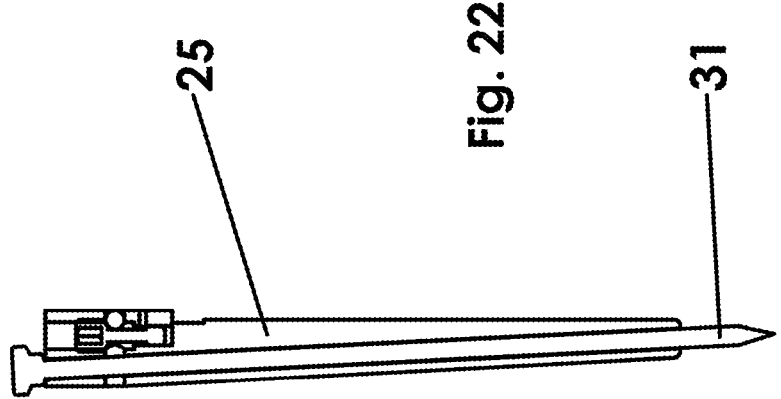
FIG. 22 illustrates a cross section of an extension blade of according to the embodiment of the apparatus according to the invention of FIG. 1, where a pin is inserted in the extension blade.

Furthermore, a blade 24 (FIGS. 1, 11 and 12 to 15) is attached to each slider 32 so that each blade 24 protrudes from the lower side 36 of the frame 29 essentially parallel to the central axis 34 of the frame 29 of the retractor 19. The retractor 19 can additionally comprise extension blades 25 whereof each one is loosenably affixable to one of the blades 24 of the retractor 19. The extension blades 25 can be fixed to the vertebrae by means of pins 31 (FIG. 22) whereof each one pin 31 extends through a bore arranged in the extension blades 25.

The above described apparatus 30 can be assembled by using respective parts of a kit, wherein a preferred embodiment of the kit comprises: a) two or more longitudinal bone anchors 11, 12; b) one or more bridging elements 20; c) two or more adjustable extension arms 16, 17; d) one or more longitudinal guiding elements 18; and e) one or more retractors 19.

Additionally, the kit can comprise one or more dilatators 21, 22, 23 which are slideable over the guiding element 18, respectively over the previously inserted dilatator 21, 22. Further, the kit can comprise two or more pins 31 for fixation of extension blades 25 of the retractor 19 to bone.

FIGS. 2 to 23 illustrate an embodiment of the method according to the invention. In a first step (FIG. 2) at least a first pair of first and second longitudinal bone anchors 11, 12 is inserted into the pedicles 2, 4 of a first and a second vertebra 6, 7 on the same side of the sagittal plane 8 and on either side of the intervertebral disc 1 to be treated. Optionally, to increase the stability of the apparatus 30 (FIG. 1) a second pair of first and second longitudinal bone anchors 11', 12' can be inserted into the pedicles 3, 5 of the first and the second vertebra 6, 7 on the other side of the sagittal plane 8 and on either side of the intervertebral disc 1 to be treated.

As illustrated in FIG. 3, in a second step a bridging element 20 is affixed to the first pair of bone anchors 11, 12. Thereto, a first clamp 13 arranged at one end of the bridging element 20 is fastened to the first bone anchor 11 and a second clamp 14 arranged at the other end of the bridging element 20 is fastened to the second bone anchor 12. The bridging element 20 further comprises a hinge 15 positioned between the first and second clamp 13, 14. At this stage, the level of the clamps 13, 14 does not matter because the level will be compensated at a later step of the method.

Optionally, at this stage of the surgical procedure a spreader can be attached to a pair of first and second bone anchors 11, 12 so that the surgeon can spread the first and second bone anchors 11, 12 to therewith move the two adjoining vertebrae 6, 7 further apart so as to enlarge the intervertebral space, particularly for facilitating insertion of an intervertebral disc replacement implant or of an intervertebral implant.

A cross beam 10 can be exemplarily attached to the first bone anchor 11' of the second pair of a first and a second bone anchor 11', 12' and to the second bone anchor 12 of the first pair of a first and a second bone anchor 11, 12. In this case the cross beam 10 is to be attached to the bone anchors 11', 12 before the bridging element 20 is attached to the bone anchors 11, 12. The cross beam 10 allows to increase the stabilization. It is possible to use only one cross beam 10. However, when necessary a second cross beam 10' (FIG. 4) can be used, which is exemplarily attached to the second pair of longitudinal bone anchors 11', 12' which is affixed to the pedicles 3, 5 of the first and second vertebrae 6, 7 on the side of the sagittal plane 8 which is opposite to the bridging element 20.

Figure 5:
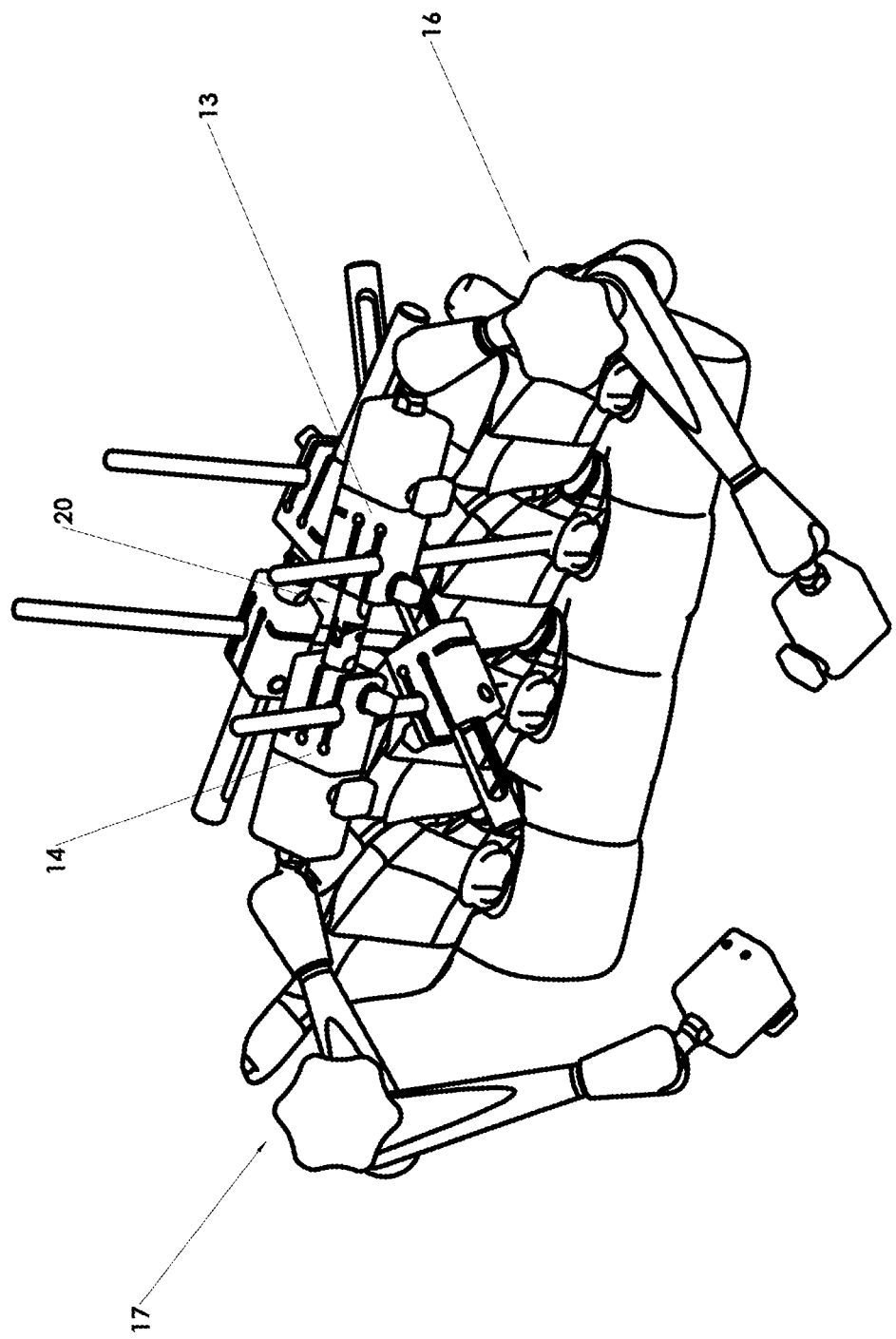
FIG. 5 illustrates a perspective view from dorsal-lateral of a portion of the spinal column with adjustable extension arms attached to the clamps according to a third step of the embodiment of the method according to the invention.

In a third step as illustrated in FIG. 5 each an adjustable extension arm 16, 17 is attached to one of the clamps 13, 14 of the bridging element 20. Each extension arm 16, 17 comprises an articulation with a locking system. Further, there are marking letters (not shown) positioned on each clamp 13, 14 and on the snap-on mountings 42 of each extension arm 16, 17 which are to be matched. The extension arms 16, 17 are to be locked once attached to the bridging element 20.

Figure 6:
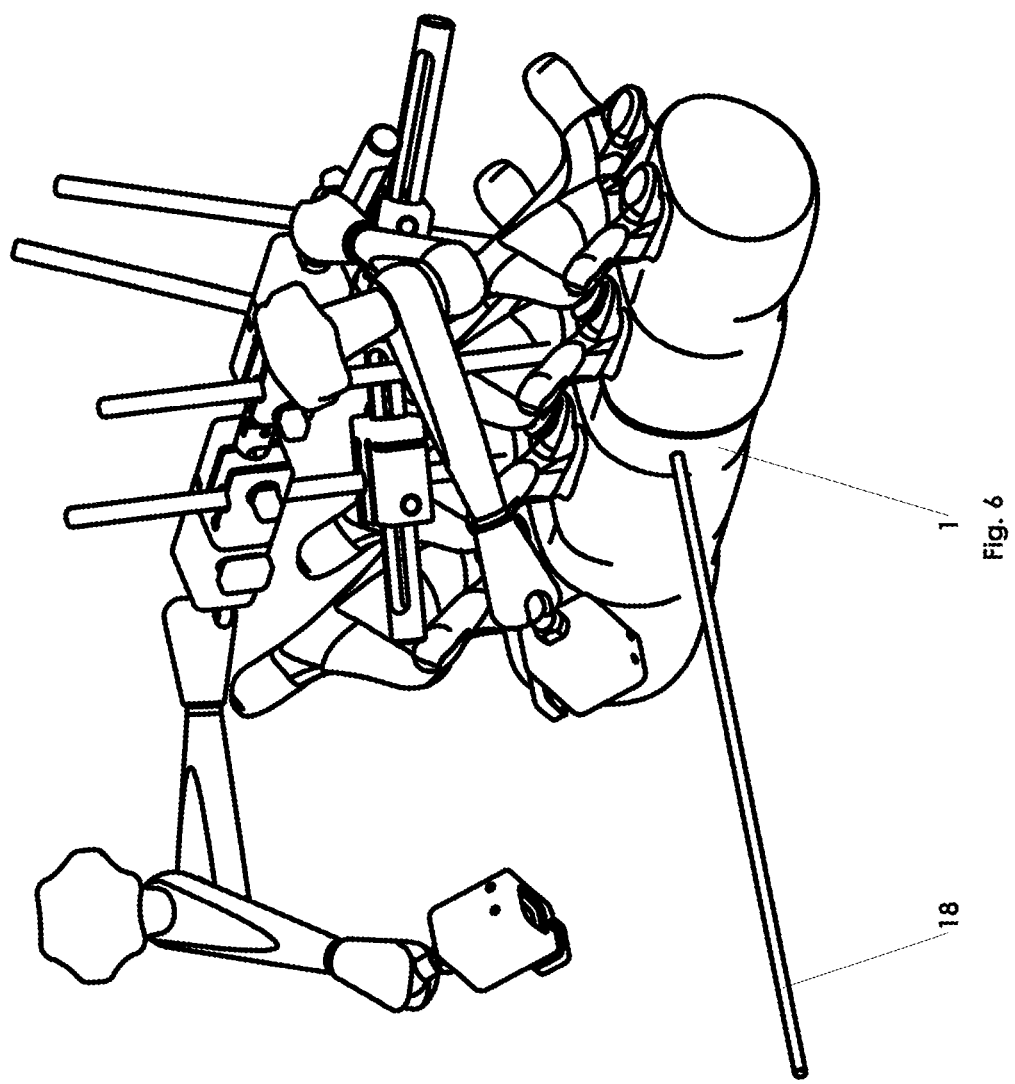
FIG. 6 illustrates a perspective view from lateral of a portion of the spinal column with a Kirschner-wire specifying the operating field according to a fourth step of the embodiment of the method according to the invention.

FIG. 6 illustrates a fourth step where the operation field is defined by introducing a longitudinal guide element 18, e.g. a Kirschner-wire into the intervertebral disc 1 to be treated at an angle between 80° and 90° with respect to the sagittal plane 8 of the patient (FIG. 2) by using X-ray. Alternatively, the longitudinal guide element 18 can be introduced into the subchondral bone of one of the vertebral bodies adjacent of intervertebral disc 1 to be treated. Thereby, only the position of the tip of the guide element 18 is important, the angle of guide element 18 will be adjusted in a further step.

Figure 7:
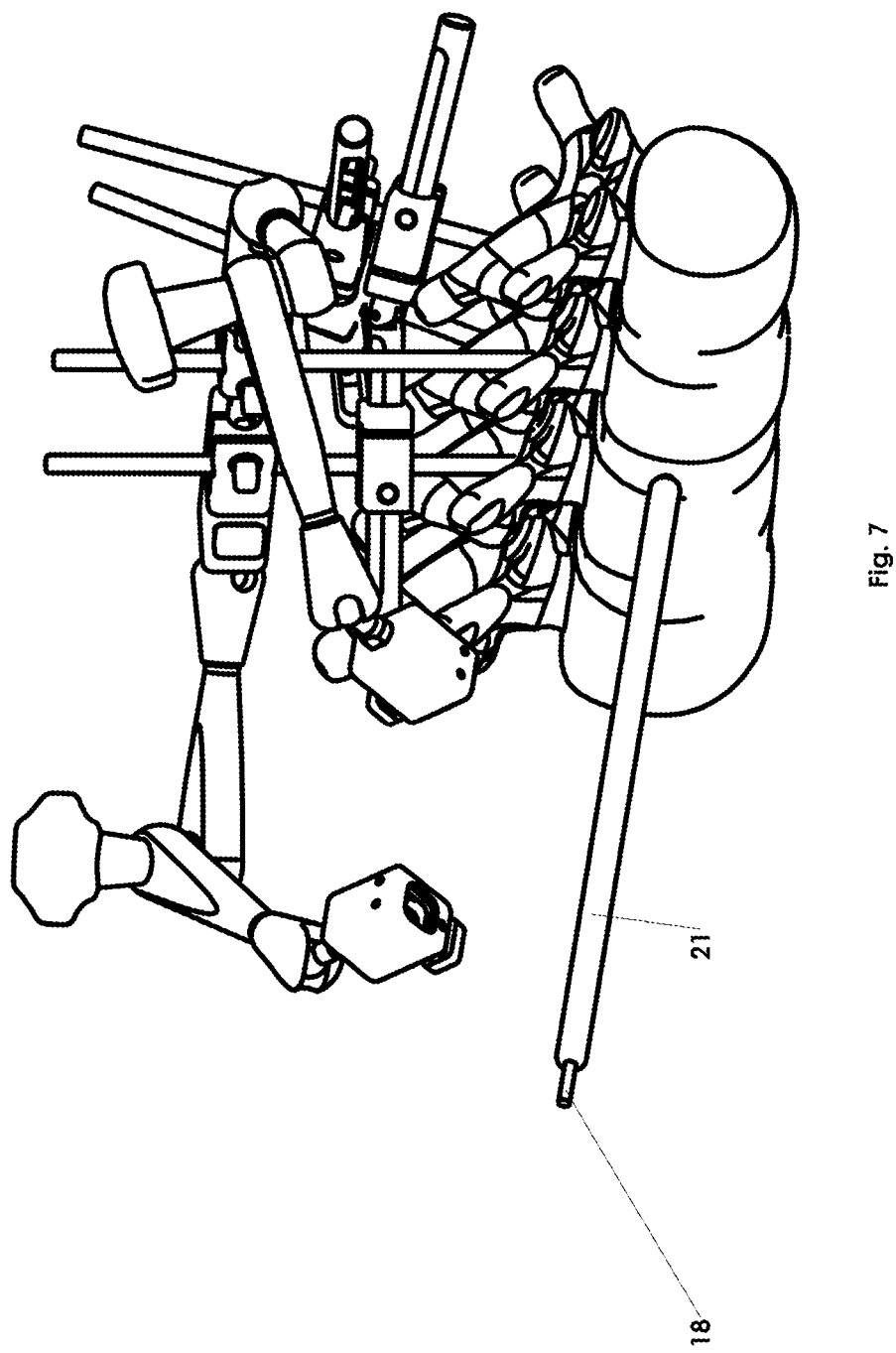
FIG. 7 illustrates a perspective view from lateral of a portion of the spinal column with a first dilatator fitted on the Kirschner-wire according to a fifth step of the embodiment of the method according to the invention.
Figure 8:
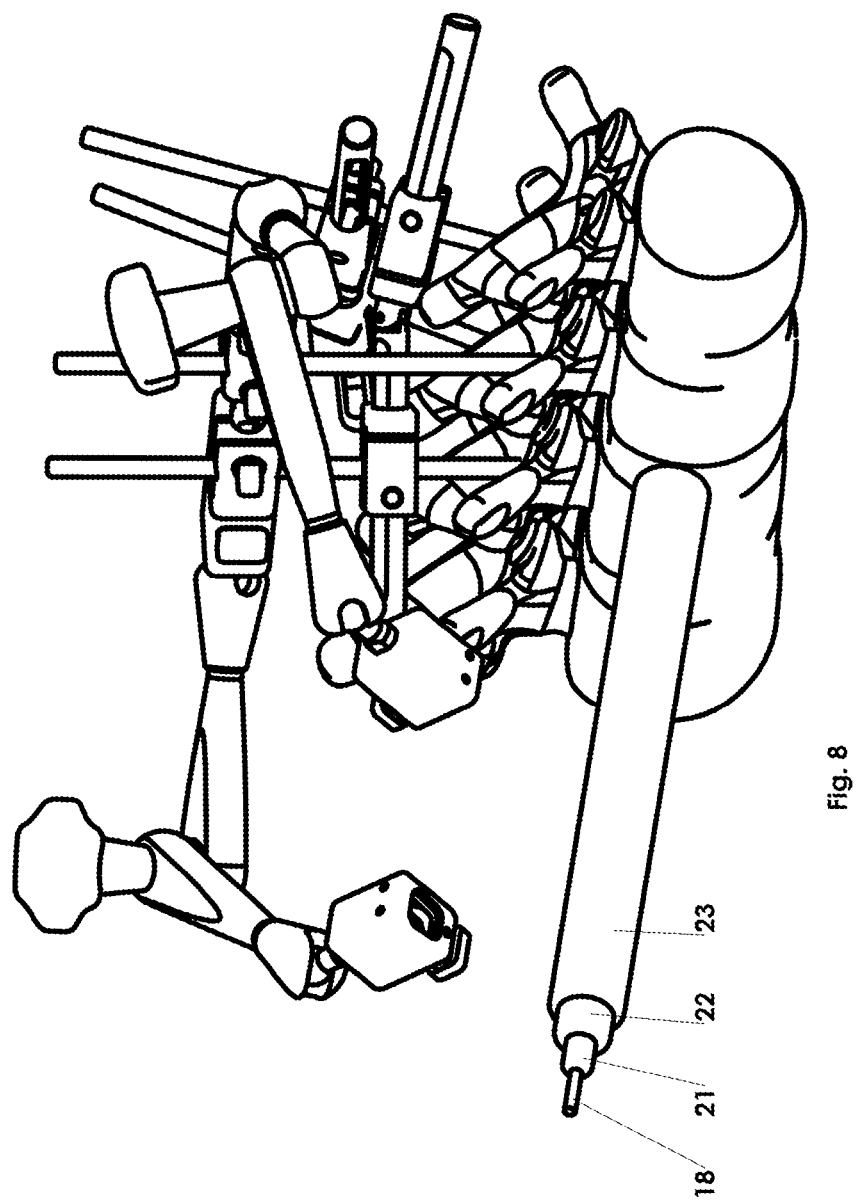
FIG. 8 illustrates a perspective view from lateral of a portion of the spinal column with a second dilatator fitted on the first dilatator according to a sixth step of the embodiment of the method according to the invention.

In a fifth step a first dilatator 21 is fitted on the longitudinal guide wire 18 as illustrated in FIG. 7. Furthermore, in a sixth step a second dilatator 22 is fitted on the first dilatator 21. Optionally, a third dilatator 23 can be fitted on the second dilatator 22 (FIG. 8).

Figure 9:
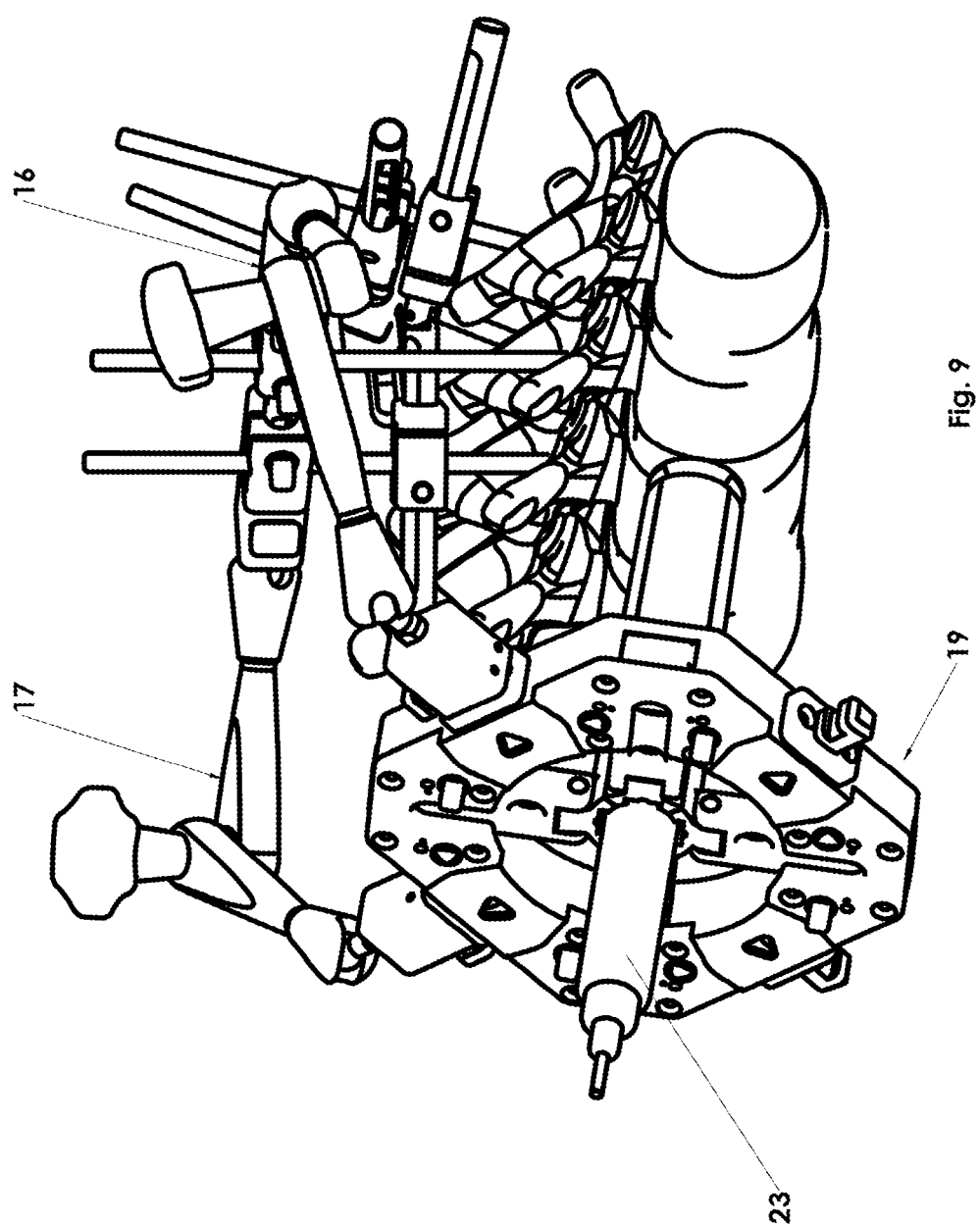
FIG. 9 illustrates a perspective view from lateral of a portion of the spinal column with a the retractor fitted on the last dilatator according to a seventh step of the embodiment of the method according to the invention.

Subsequently, in a seventh step as illustrated in FIG. 9 the retractor 19 is fitted on the outermost, i.e. the third dilatator 23 in the present exemplary embodiment. The lower sections of the extension arms 16, 17 are locked to the retractor 19 with a locking system. Further, there are marking letters (not shown) positioned on the snap-on mountings 42 of the extension arms 16, 17 and on the retractor 19 which are to be matched. The lower sections of the extension arms 16, 17 are locked with a button on their locking devices. In this seventh step the retractor 19 can be adjusted in the proper position. After this adjustment is completed, the locking systems on each extension arm 16, 17 are tightened. The position of the retractor 19 for the operation is now fixed and should not be modified. Any further manipulation of the extension arms 16, 17 must be avoided.

Figure 10:
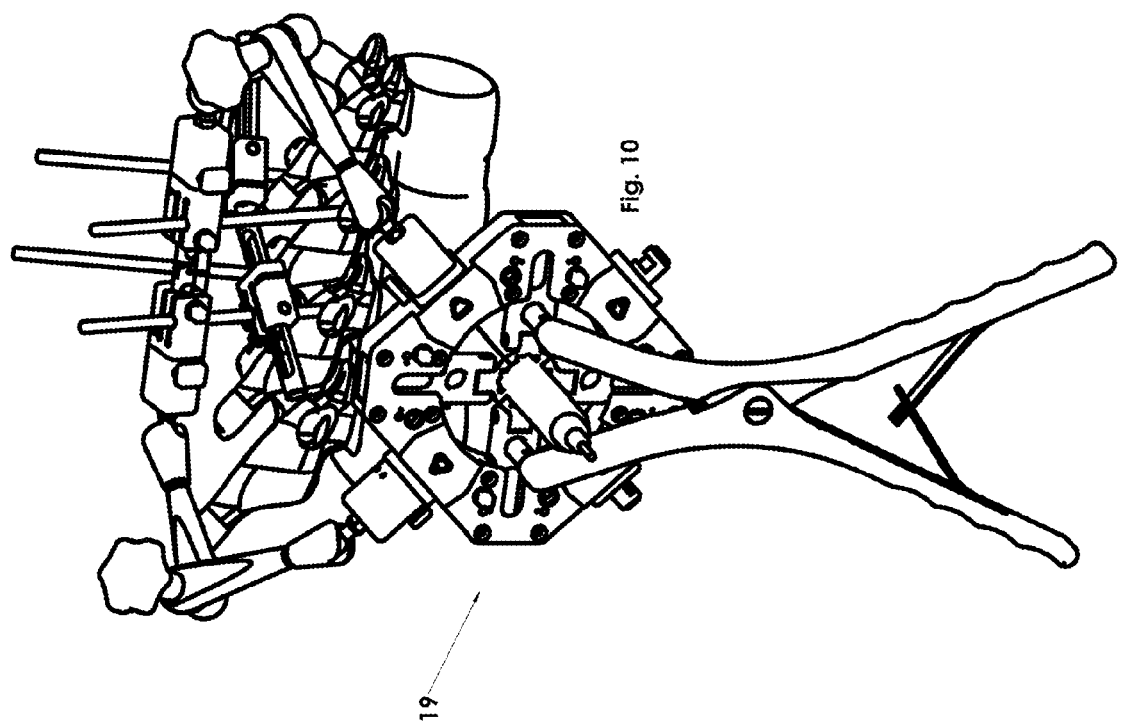
FIG. 10 illustrates a perspective view from lateral of the retractor of the embodiment of the apparatus according to the invention of FIG. 1 when being opened with a separating tool.
Figure 11:
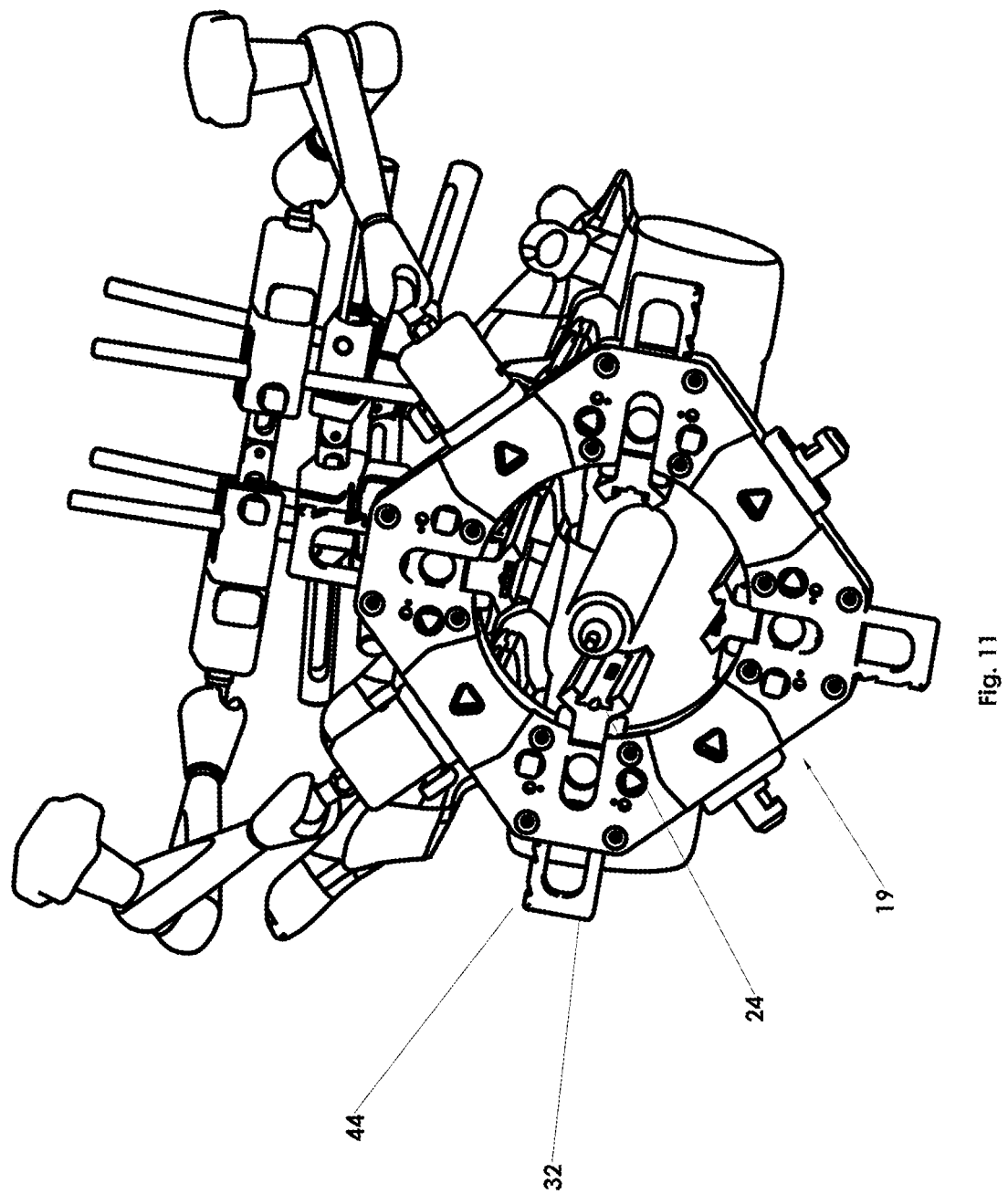
FIG. 11 illustrates a perspective view from lateral of the retractor of the embodiment of the apparatus according to the invention of FIG. 1 when being fully opened.

As shown in FIG. 10 the retractor 19 can be opened with a special separating tool. The maximum opening range is the inner ring of the retractor 19. As the retractor 19 is opened, each click indicates a potential locking position for the blades 24 (FIG. 11) of the retractor 19. FIG. 11 illustrates the fully opened retractor 19.

Figure 12:
FIG. 12 illustrates a lateral view of the extension blades according to the embodiment of the apparatus according to the invention of FIG. 1, where the extension blades are attached to a special screwdriver.
Figure 13:
FIG. 13 illustrates a perspective view from lateral of the extension blades inserted in the blades of the retractor according to an eighth step of the embodiment of the method according to the invention.
Figure 14:
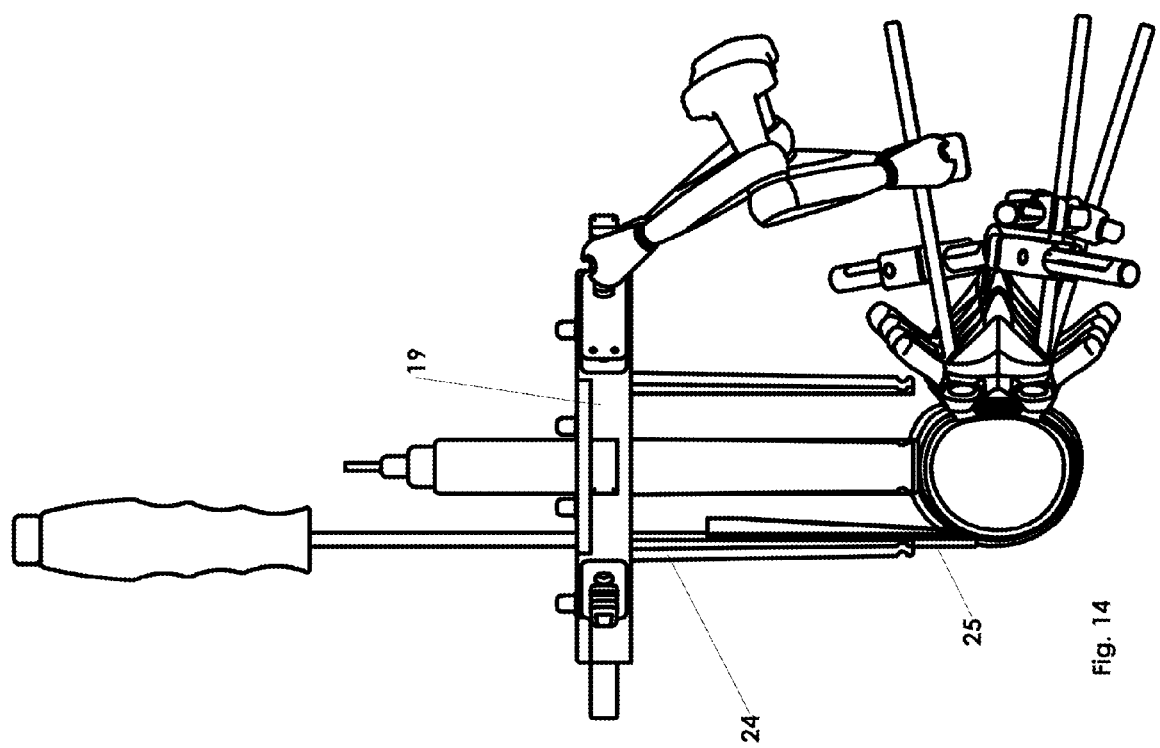
FIG. 14 illustrates a side view of the retractor during insertion of the extension blades in the blades of the retractor according to the eighth step of the embodiment of the method according to the invention.

Before insertion of the extension blades 25 a screwdriver is attached to the extension blades 25 as illustrated in FIG. 12. Then, in an eighth step as shown in FIG. 13 the extension blades 25 are inserted in the blades 24 of the retractor 19. It is possible to pre-fix the extension blades 25 on the blades 24 of the retractor 19 with a screwdriver as shown in FIG. 14. The screwdriver has to be removed when the extension blades 25 are in their position. If necessary the retractor 19 could be closed and reopened depending on the anatomical situation.

Figure 15:
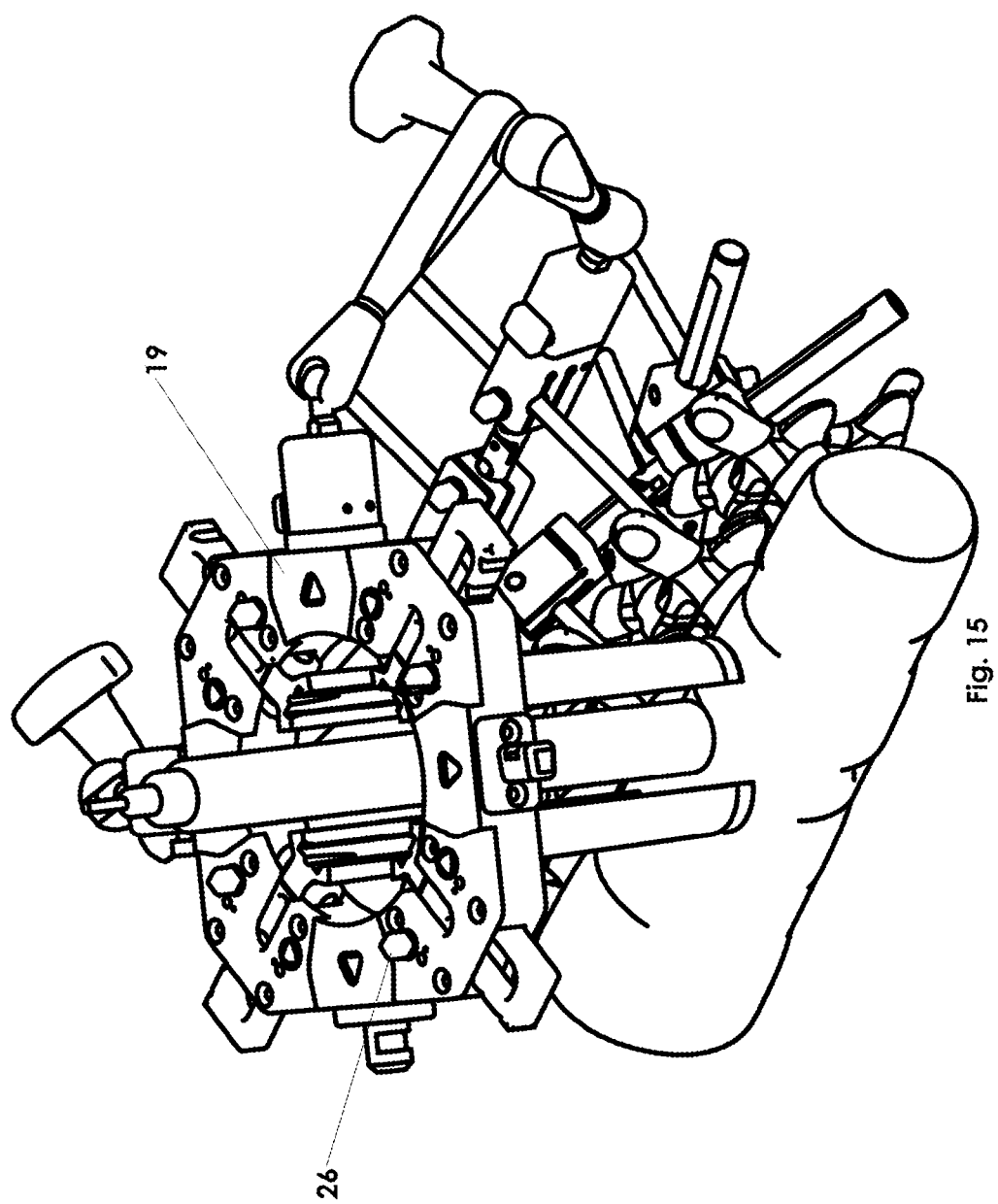
FIG. 15 illustrates a perspective view from dorsal-lateral of a portion of the spinal column with a light adapter attached to the retractor according to a ninth step of the embodiment of the method according to the invention.

In a ninth step as illustrated in FIG. 15 a light adapter 26 can be attached to the retractor 19 on one of the free positions of the retractor locking system. The light adapter 26 can be used to fix a standard surgical lightning system.

Figure 16:
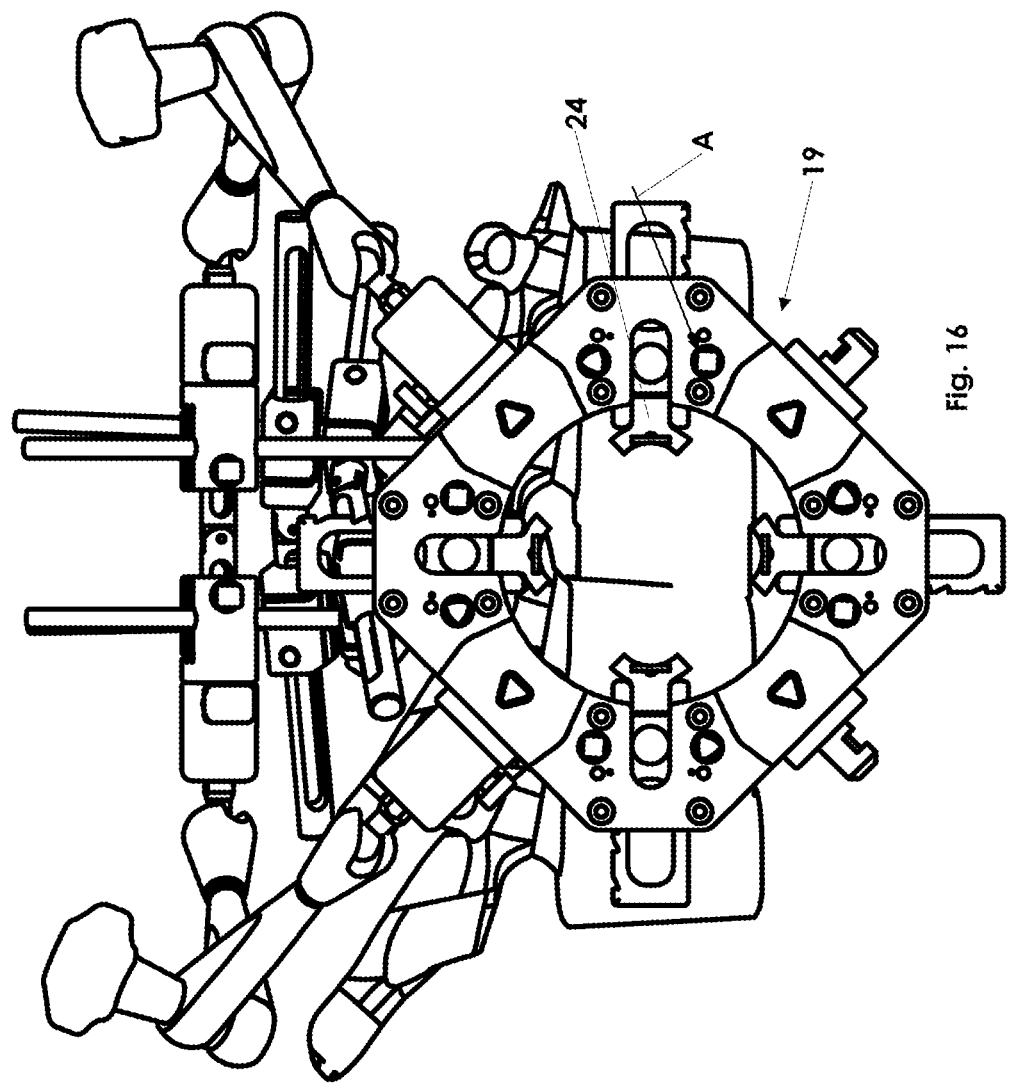
FIG. 16 illustrates a lateral view of the retractor when being closed according to a tenth step of the embodiment of the method according to the invention.

In an tenth step as illustrated in FIG. 16 the retractor 19 is closed on the positions indicated by arrows A. It is possible to lock or unlock each individual blade 24. If it is necessary to reopen the retractor 19, it is possible to do that with a special separating tool (not shown).

Figure 20:
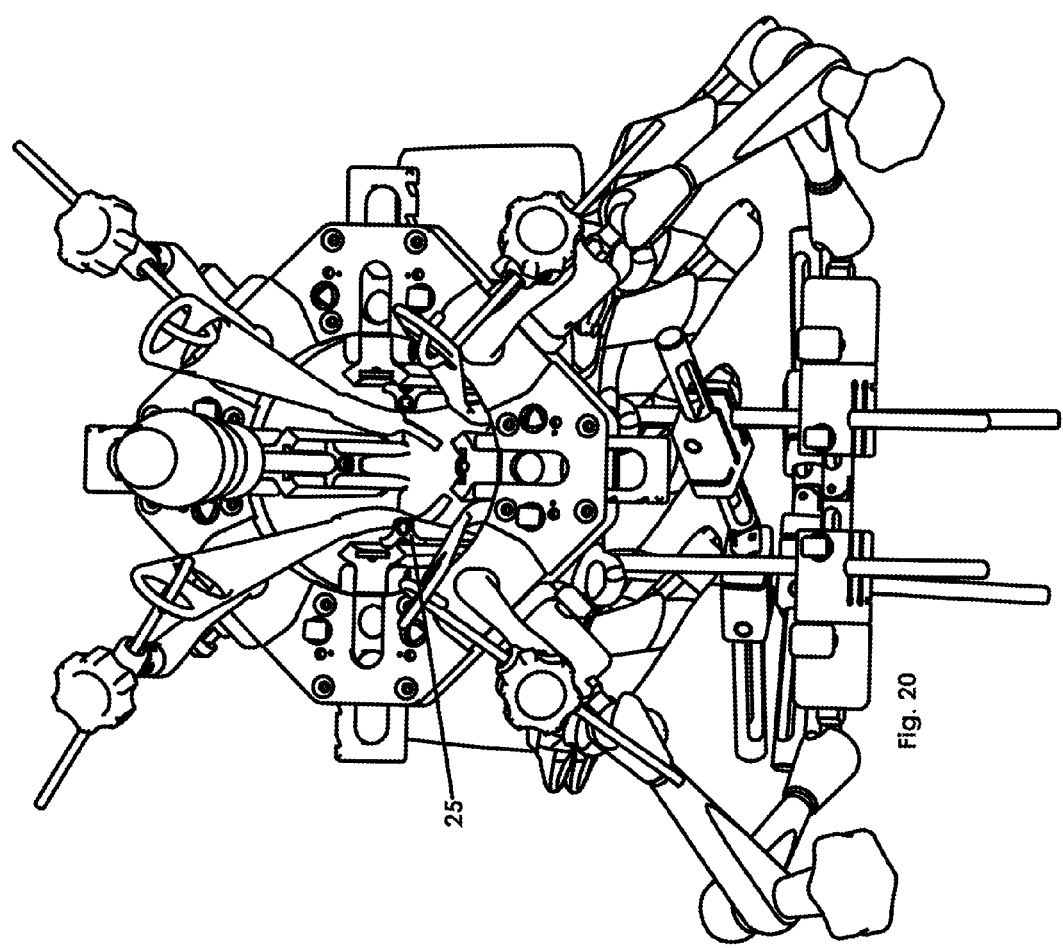
FIG. 20 illustrates a perspective view from lateral of the retractor during fixation of the extension blades according to the embodiment of the method according to the invention of FIG. 17.
Figure 21:
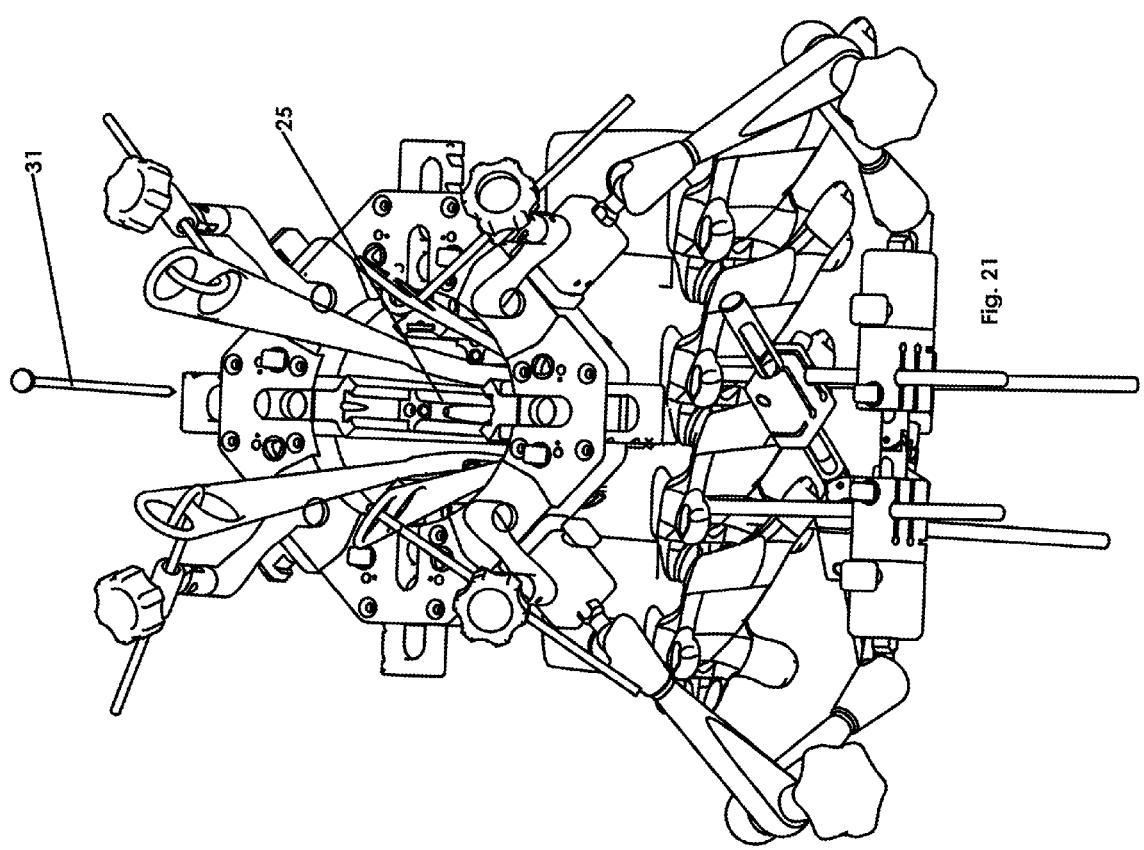
FIG. 21 illustrates a perspective view from lateral of the retractor during fixation of the extension blades with pins according to the embodiment of the method according to the invention of FIG. 17.

Subsequently, as illustrated in FIG. 20 the extension blades 25 can be fixed in their final position by using a screwdriver. Thereafter, the extension blades 25 can be fixed in a sixteenth step (FIGS. 21 and 22) with pins 31 after removing the screwdriver.

Figure 17:
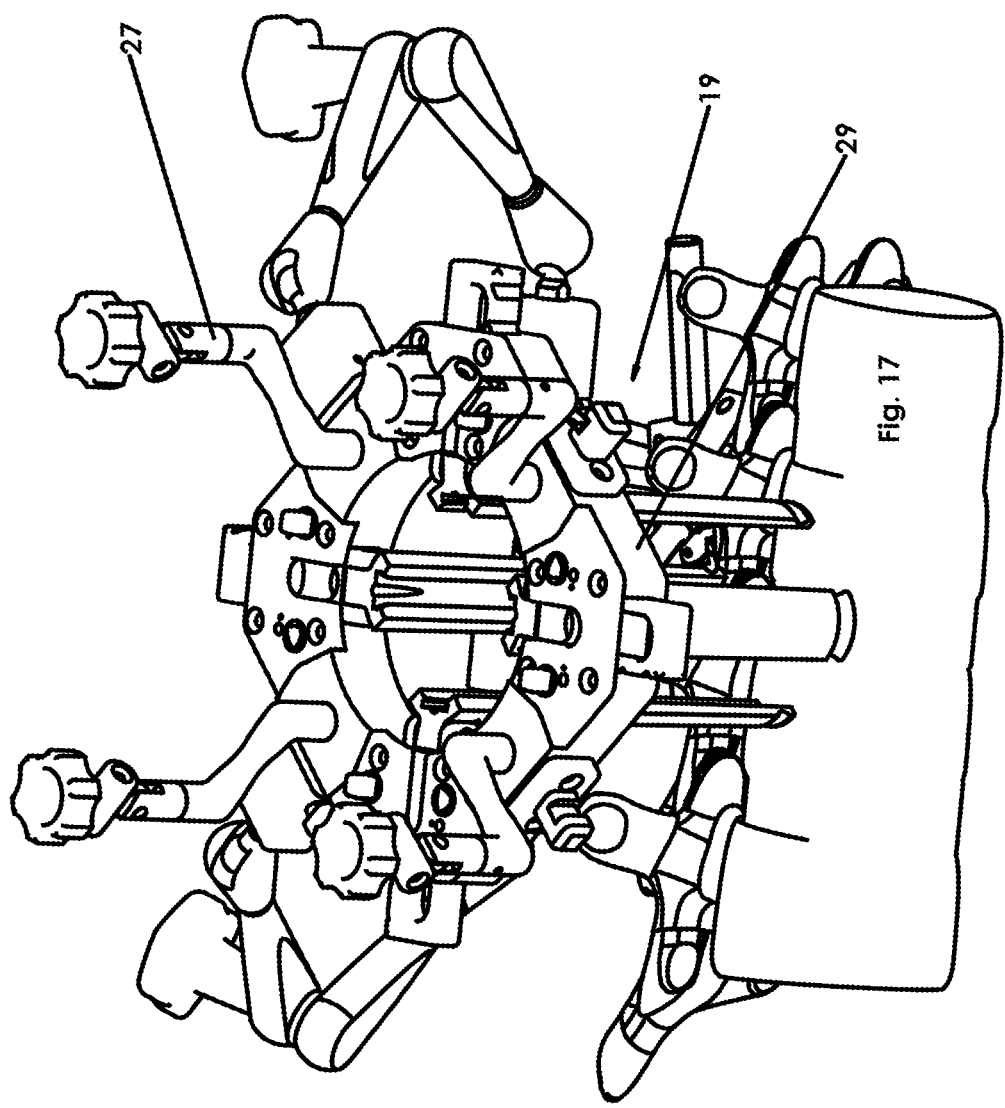
FIG. 17 illustrates a perspective view from dorsal-lateral of the retractor with four Hohmann-adpaters attached thereto according to another embodiment of the method according to the invention.
Figure 18:
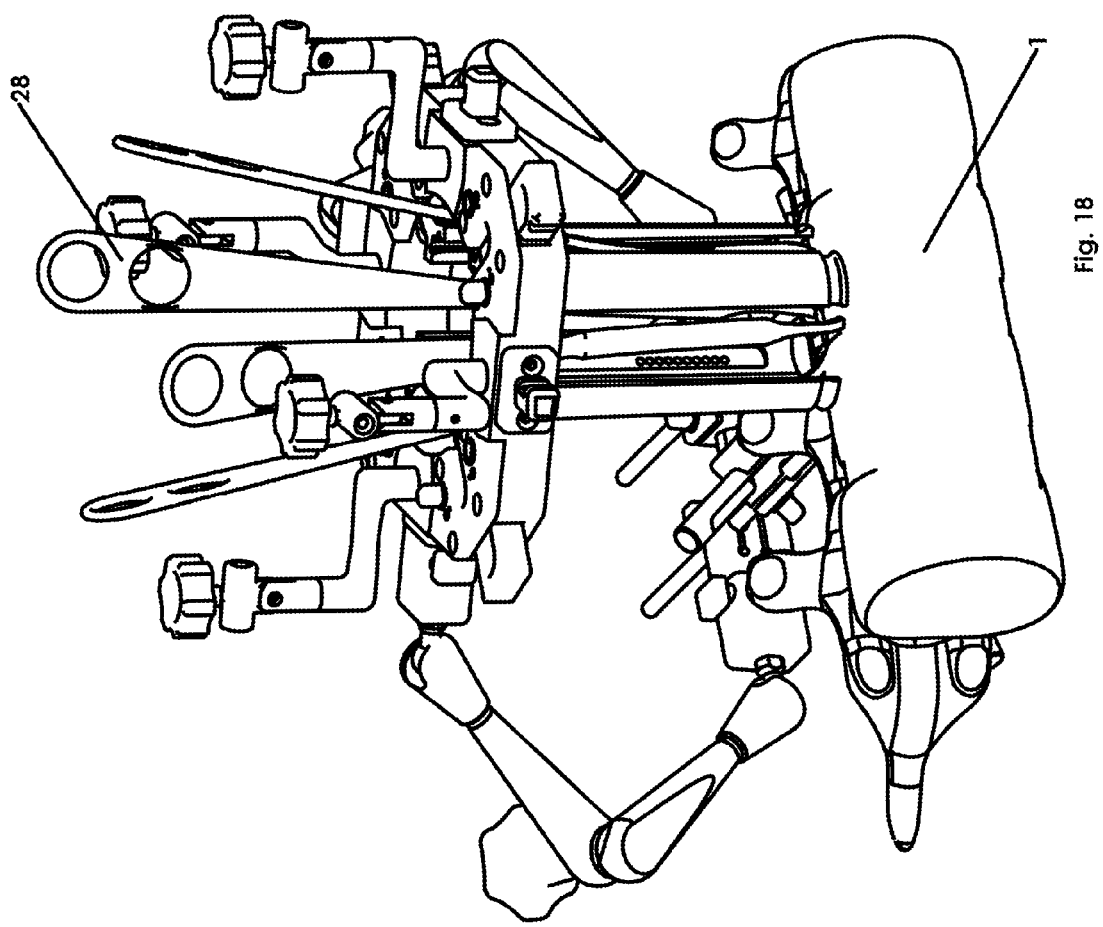
FIG. 18 illustrates a perspective view from dorsal of the retractor with four Hohmann-levers attached to the Hohmann-adapters during preparation of the operation field according to the embodiment of the method according to the invention of FIG. 17.
Figure 19:
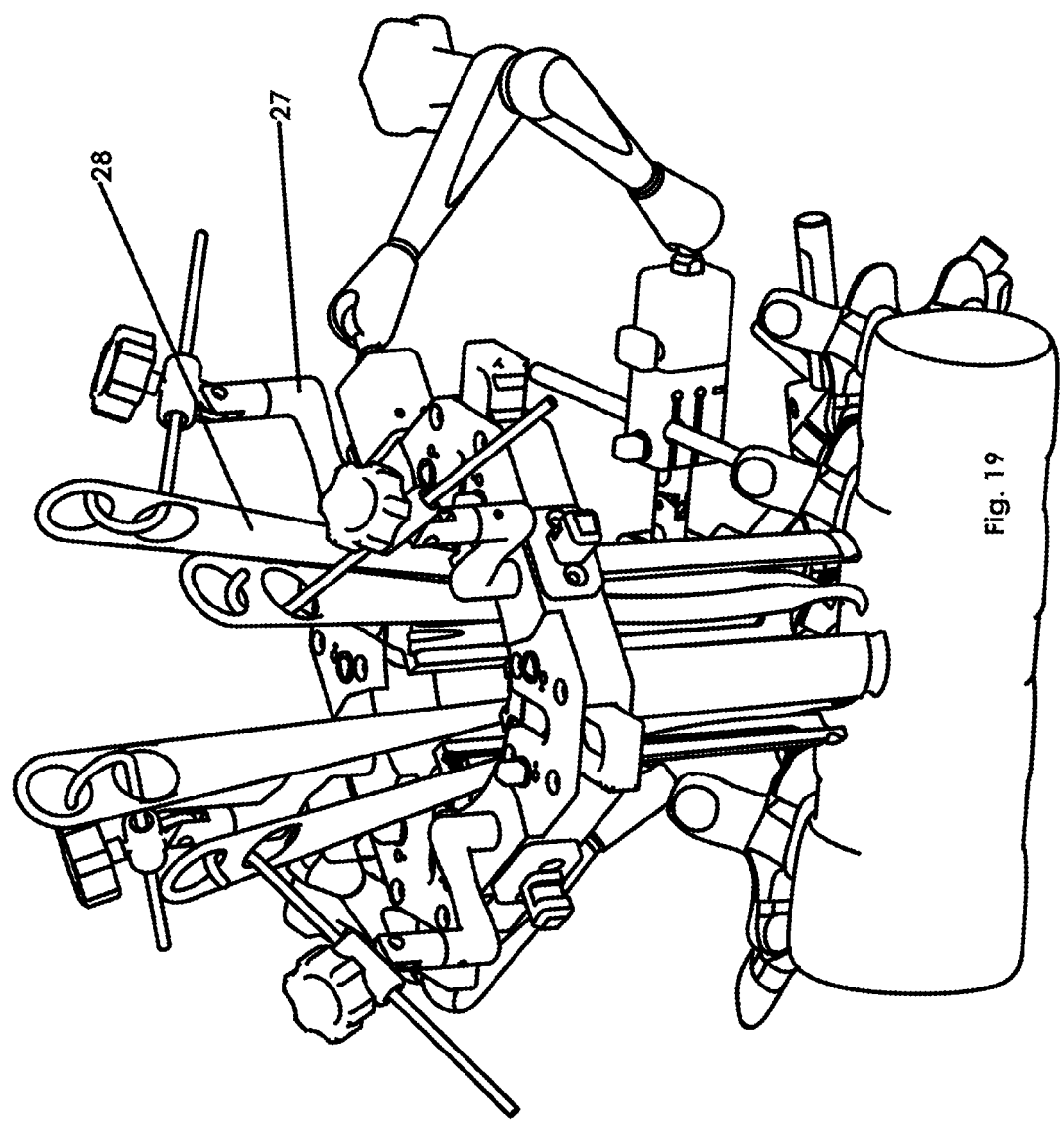
FIG. 19 illustrates a perspective view from dorsal-lateral of the retractor with four Hohmann-levers fixed to a Hohmann-adapter each according to the embodiment of the method according to the invention of FIG. 17.

In another embodiment of the method according to the invention—if desired by the surgeon—Hohmann-levers 28 can be used for the surgical procedure as illustrated in FIGS. 18-21. In this case the Hohmann-levers 28 are used to prepare the operation field before the extension blades 25 are fixed in their final position. As illustrated in FIG. 17, the Hohmann-adapters 27 can be attached to the frame 29 of the retractor 19, exemplarily in four positions. Due to the close quarters of the frame 29, two vis-à-vis positions are recommended. Subsequently, each a Hohmann-lever 28 can be used to prepare the operation field so that no tissue remains on the intervertebral disc 1 and the nerves are moved outside the operation field. Then, as illustrated in FIG. 19 each Hohmann-lever 28 can be fixed to the respective Hohmann-adapter 27 after the Hohmann-levers 28 have been softly tapped in with a hammer.

Figure 23:
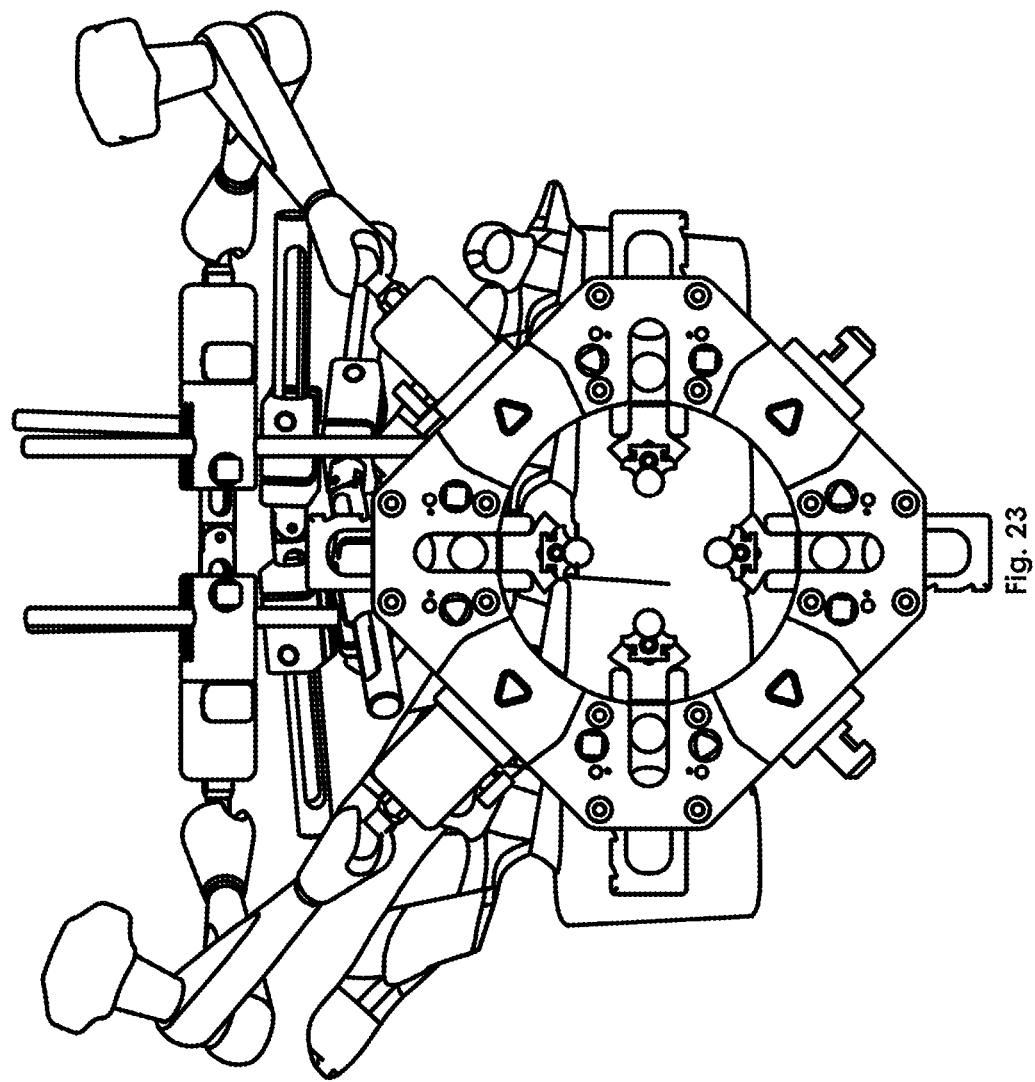
FIG. 23 illustrates a top view of the retractor which the Hohmann-levers removed according to the embodiment of the method according to the invention of FIG. 17.

The extension blades 25 can then be fixed in their final position by using a screwdriver (FIG. 20). Thereafter, the extension blades 25 can be fixed (FIGS. 21 and 22) with pins 31 after removing the screwdriver. For the subsequent intervertebral disc operation the Hohmann-levers 28 must be removed (FIG. 23).

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims.

What is claimed is:

1. A method for the removal of intervertebral discs or parts thereof comprising the following steps:
   inserting a first longitudinal bone anchor into one of the two pedicles of a first vertebra on one side of the intervertebral disc to be treated;
   inserting a second longitudinal bone anchor into one of the two pedicles of a second vertebra on the same side or the other side of the intervertebral disc to be treated;
   bridging the first and second longitudinal bone anchor by a bridging element comprising a first and second clamp connected by a hinge;
   attaching adjustable extension arms to each of the two clamps;
   introducing a longitudinal guiding element into
      (i) the intervertebral disc to be treated, or
      (ii) the subchondral bone of one of the vertebral bodies adjacent of intervertebral disc to be treated,
   at an angle α with respect to the sagittal plane of the patient, the angle α being in the range of 80°-90°;
   fixing a retractor on the longitudinal guiding element orthogonal to an axis defined by the longitudinal guiding element;
   connecting the free ends of the extension arms to the retractor;
   immobilizing the extension arms in order to obtain a rigid assembly; and
   using the retractor as an anatomically positioned platform for performing the removal of the intervertebral disc to be treated or parts thereof.

2. The method according claim 1, wherein the longitudinal guiding element is a Kirschner-wire or a bone pin.

3. The method according claim 1, wherein the longitudinal guiding element comprises a navigational tool.

4. The method according to claim 1, wherein four or more longitudinal bone anchors are inserted into the pedicles of the first and second vertebrae.

5. The method according to claim 1, wherein the longitudinal bone anchors are inserted into the transition zone of the superior facet joint of the vertebra.

6. The method according to claim 1, wherein the longitudinal bone anchors are inserted into the neck of the facet joint.

7. The method according to claim 1, wherein the longitudinal bone anchors and the longitudinal guiding element are inserted subcutaneously.

8. The method according to claim 1, comprising a further step:
   using the retractor as an anatomically positioned platform for implanting an artificial disc or an osteosynthetic cage into the intervertebral space of the removed intervertebral disc.

9. The method according to claim 1, comprising after insertion of the first and second longitudinal bone anchors into the pedicles of the first and second vertebrae a further step of:
   spreading the first and second bone anchors to therewith move the two adjoining vertebrae further apart by using a spreader to enlarge the intervertebral space, particularly for facilitating insertion of an intervertebral disc replacement implant or of an intervertebral implant.

10. The method according to claim 1, wherein the hinge of the bridging element is locked using a reversibly lockable locking mechanism.

11. The method according to claim 1, further comprising, before the retractor is fixed on the longitudinal guiding element, a step of fitting a first tubular dilatator onto the longitudinal guiding element.

12. The method according to claim 11, further comprising a step of subsequently and telescopically pushing one or more further tubular dilatators over the first dilatator.

13. The method according to claim 1, further comprising after use of the retractor as an anatomically positioned platform for performing the removal of the intervertebral disc to be treated or parts thereof, a step of pulling or pushing sliders which are slideably arranged on the retractor towards or away from the guiding element until a desired opening as an operation field is achieved.

14. The method according to claim 13, further comprising an additional step of inserting extension blades in blades attached to the sliders of the retractor.

15. The method according to claim 14, further comprising an additional step of inserting a pin in each extraction blade to affix the same in position relative to the retractor.

* * * * *